(12) United States Patent
Boëthius

(10) Patent No.: US 7,022,125 B2
(45) Date of Patent: Apr. 4, 2006

(54) METHOD AND HEMOSTATIC PATCH FOR EFFECTING LOCAL HEMOSTASIS

(75) Inventor: Jörgen Boëthius, Täby (SE)

(73) Assignee: Perlei Medical Incorporated, Melbourne, FL (US)

( * ) Notice: Subject to any disclaimer, the term of this patent is extended or adjusted under 35 U.S.C. 154(b) by 0 days.

(21) Appl. No.: 09/957,887

(22) Filed: Sep. 21, 2001

(65) Prior Publication Data

US 2002/0049471 A1    Apr. 25, 2002

(30) Foreign Application Priority Data

Sep. 22, 2000  (EP)  ................. 00120728

(51) Int. Cl.
*A61B 17/08*    (2006.01)

(52) U.S. Cl. ..................... 606/151; 606/213

(58) Field of Classification Search ........... 606/151, 606/213, 214; 604/304, 2; 424/443–449
See application file for complete search history.

(56) References Cited

U.S. PATENT DOCUMENTS 5,645,849 A * 7/1997 Pruss et al. .............. 424/426
6,548,729 B1 * 4/2003 Seelich et al. ............ 602/48

FOREIGN PATENT DOCUMENTS

| DE | 41 15 453 | 11/1992 |
|---|---|---|
| EP | 0 090 997 | 10/1983 |
| EP | 0 090 997 | 12/1983 |
| JP | 54 098091 | 8/1979 |
| WO | 90/13320 | 11/1990 |
| WO | WO 90 13320 | 11/1990 |
| WO | 93/06855 | 4/1993 |
| WO | WO 93 06855 | 4/1993 |
| WO | 93/24086 | 12/1993 |
| WO | WO 93 24086 | 12/1993 |
| WO | 95/12371 | 5/1995 |
| WO | WO 95 12371 | 5/1995 |
| WO | 96/40033 | 12/1996 |
| WO | WO 96 40033 | 12/1996 |

OTHER PUBLICATIONS

Stephen King et al. Surgery vol. 109, No. 1, pp. 76-84.*
Saliba et al. British Journal of Plastic Surgery (2000, 53 pp. 42-45).*
Rodeheaver et al. Mechanical Cleansing of Contaminated Wounds with a Surfactant vol. 129, Mar. 1975, pp. 241-245.*
Blairex Sterile Wound Wash Saline, Marketing Intellegence Servic , LTD, copyright 2001.*
Looks et al. Wound Forum "Trial of Tenderwet to cleanse poorly healing wounds", Apr. 1997.*
Derwent Abstracts XP 002160780 (JP 54-098091)—Unitika Ltd.
Pharmacia, Nov. 2000; pp. 1-2.

* cited by examiner

*Primary Examiner*—Eduardo C. Robert
*Assistant Examiner*—Jessica R. Baxter

(57) ABSTRACT

In a method for effecting hemostasis of a bleeding wound, an antifibrinolytic agent is applied to a substrate and the substrate with the antifibrinolytic agent applied thereto is placed onto the bleeding wound. A hemostatic patch has a substrate that is impregnated with the antifibrinolytic agent and is preferably enclosed in a foil package and is ready to use when the package is opened.

40 Claims, No Drawings

METHOD AND HEMOSTATIC PATCH FOR EFFECTING LOCAL HEMOSTASIS

BACKGROUND OF THE INVENTION

1. Field of the Invention

The invention relates to a method and a hemostatic patch for local and spontaneous hemostasis for treating bleeding wounds that are the result of injuries or surgery.

2. Description of the Related Art

It is known to use patches or compresses etc. made of cellulose, gelatin, or collagen for effecting hemostasis of bleeding wounds, caused by injury or by surgical intervention. Also known is the application of fibrin adhesives or thrombin.

In the case of neurosurgical and microsurgical operations, it is customary to employ sponges or compresses which are impregnated or soaked with physiological saline solutions for effecting hemostasis. Trying to effect hemostasis in this way is usually time-consuming and requires a large number of sponges or compresses.

The use of medical sponges or compresses is moreover limited because hemostasis can be effected only over a limited period of time.

International patent document WO 93/24086 describes a sponge whose adsorbent textile part is comprised of several layers of textile material and has an x-ray-opaque string. Because of the multi-layer configuration of the textile part the sponge is relatively thick and is therefore not suitable for neurosurgical and microsurgical operations.

Hemostasis refers to the action of stopping the bleeding of a wound and is the result of interaction of various functions: vasocontraction as well as vasoretraction, aggregation of platelets, as well as blood coagulation or clotting. These various functions can be assisted by administering substances which directly or indirectly affect hemostasis, such as vitamin K, astringent agents, thrombin, high-molecular colloids, fibrin foam as well as blood transfusions, substitution of coagulation factors as well as local cooling or the like.

Blood coagulation is a very complex process which takes place in several stages. The end result is the formation of insoluble fibrin from the fibrinogen which is contained in the blood plasma. This process of fibrin formation is catalyzed by thrombin in interaction with calcium ions. Approximately 30 different factors interact to accomplish blood coagulation, inter alia, the coagulation factors of the blood plasma and numerous platelet factors.

Hemostasis occurs in two stages: primary hemostasis and secondary hemostasis. In the initial stage, which is generally referred to as primary hemostasis, accumulation and aggregation of platelets occur and the resulting "plug" initially closes the wound to slow down the loss of blood. The accumulation of the platelets and their aggregation are controlled primarily by thromboxane A2. The initial closure of the wound is also assisted by so-called vasoconstricting substances, for example, serotonin, which provide a reduction of the opening of the wound. The aggregation or fusion of the platelets results in the release of the so-called platelet factor 3 which plays an important role in the second stage of hemostasis (secondary hemostasis)—the blood coagulation. The process of secondary hemostasis encompasses the sequential activation of plasma coagulation factors leading within five to seven minutes to the formation of a mechanically stable fibrin thrombus around the initial platelet plug.

Another approach to suppress bleeding is the use of antifibrinolytic agents, i.e., agents that act to prevent dissolution of fibrin clots. As is known in the medical field, such substances are administered in the form of a solution to be injected or in the form of tablets or pills to be administered orally in the case of hyperfibrinolysis, i.e., increased fibrinolysis as a result of increased levels of plasminogen. They are used to treat serious bleeding, for example, after dental surgery (particularly in patients with hemophilia) or other kinds of surgery and are also given before an operation to prevent serious bleeding in patients. The maximum effect of the application of an antifibrinolytic agent, for example, by means of injection, is reached after about six hours. Side effects such as nausea, vomiting, or diarrhea are observed; these side effects will subside when the concentration of the substance in the blood decreases.

SUMMARY OF THE INVENTION

It is an object of the present invention to provide a local hemostatic wound treatment effecting improved hemostasis of bleeding wounds resulting from injuries, e.g., cuts, lacerations, abrasions etc, and/or surgery.

According to the present invention this is achieved by a method according to which an antifibrinolytic agent is applied to a substrate and the substrate so prepared is applied to a bleeding wound.

The present invention also relates to a hemostatic patch comprising a substrate and a means for effecting hemostasis contained in the substrate, the means for effecting hemostasis being in the form of an antifibrinolytic agent, wherein at least that part of the substrate to be placed onto the wound contains the antifibrinolytic agent and/or releases such an antifibrinolytic agent.

Antifibrinolytic compounds are known in the art and include, as examples, $\epsilon$-aminocaproic acid, tranexamic acid, and p-aminomethyl benzoic acid, which are all lysine analogs, as well as aprotinin, which is a representative of the class of kinins characterized by the presence of a certain sequence of nine amino acids. Lysine analogs are compounds that have a structure similar to lysine lacking the $\alpha$-amino group. Lysine analogs and kinins are known to suppress plasmin activity. The antifibrinolytic agent according to the invention, which can contain one or more antifibrinolytic compounds, for example, those mentioned above, can be applied to the substrate as such or can be applied as a solution.

The solution can be an aqueous solution but solvents other than water suitable for dissolving the antifibrinolytic agent or compounds are possible, wherein, of course, the solvents must be selected such that there is no negative interaction between the solvent and the antifibrinolytic agent and, in particular, with the desired goal of effecting hemostasis. Solvents suitable for this purpose are, for example, physiological saline solutions. Others will be apparent to a person skilled in the art.

The antifibrinolytic agent can be applied as a concentrated or saturated solution or any solution less than saturated as long as the desired rapid hemostasis is still effected. Especially effective concentration ranges of the lysine analogs contained in the antifibrinolytic agent are 50 to 500 mg, a preferred range being 100 to 250 mg, in 1 ml water, wherein a single lysine-analog compound or a mixture of lysine-analog compounds can be used. In the case of kinins such as aprotinin an effective concentration range in the antifibrinolytic agent is 10,000 to 150,000 KIU per 1 ml water. In the case of an antifibrinolytic agent containing a mixture of lysin analogs and kinins, the above concentrations are also applicable, respectively.

Surprisingly, it was found that a substrate, for example, a wound dressing or medical sponge or the like having applied thereto an antifibrinolytic agent, for example, by being impregnated therewith causes rather spontaneous hemostasis when applied locally to a bleeding wound, be it caused by an injury or a surgical intervention. In the case of surgery, a considerable improvement of the operating conditions and a gentle tissue treatment result. In the case of injury-related wounds, rapid hemostasis reduces the risk of infection and generally improves healing. The substrates or hemostatic patches are applied only temporarily on the wound for the purpose of controlling bleeding and effecting hemostasis and replaced as needed with a fresh substrate or patch; when the wound has stopped bleeding or bleeding has been suppressed to the desired extent, the patches are removed from the wound, and the required further wound treatment or surgical treatment is then initiated. The number of patches required to stop bleeding varies, of course, with the size, type and location of the wound.

In a preferred embodiment of the invention, the antifibrinolytic agent is tranexamic acid or a tranexamic acid solution. In accordance with the present invention, tranexamic acid or a solution thereof is applied to a substrate or sponge or the like. Preferably, an aqueous concentrated solution of tranexamic acid is applied to the substrate; the solution can be applied by soaking the substrate in the solution or impregnating the substrate with the solution. It was found that a concentration of 50 to 150 mg, in particular, 80 to 120 mg, and especially 100 mg of tranexamic acid in 1 ml water, was particularly effective.

It is possible to apply the antifibrinolytic agent such to the substrate that the substrate is essentially dry when placed onto the wound; the substrate is then irrigated with a solvent to facilitate release of the antifibrinolytic agent into the wound.

The substrate is understood in the context of the invention to include any type of medical compress, patch, sponge, pad, swab, dressing or the like as they are conventionally used in the medical field for wound treatment. The substrate is preferably made of cotton and/or cellulose-based material (viscose or rayon) and is preferably in the form of an absorbent woven or non-woven textile product.

The substrate may have a retaining string or tether attached thereto which allows its use in endoscopic surgery by providing a means for pulling the substrate out of the endoscopic wound and also facilitates its removal from other types of wounds. Also, an x-ray-opaque string may be attached to the substrate as a safety measure to enable locating the substrate post-operatively.

The invention also relates to a combination of a hemostatic patch and a disposable seal-tight envelope in which the hemostatic patch is sealed so as to be sterile and to stay moist until use. The hemostatic patch, as defined above, comprises a substrate containing a means for effecting hemostasis in the form of an antifibrinolytic agent as described above and applied to the substrate in the different ways disclosed above.

Seal-tight envelopes to preserve a product, keep it sterile, and/or keep it moist are known in the art and need not be described in more detail in this context.

As disclosed above the substrate may have a retaining string or an x-ray-opaque string attached thereto.

The invention includes also a medical kit for hemostasis, comprised of one or more substrates, as defined above, and a means for effecting hemostasis in the form of a solution of an antifibrinolytic agent. A solution of the antifibrinolytic agent is provided in ampules, bottles, and the like. As mentioned above, a preferred antifibrinolytic agent is tranexamic acid. The substrate is soaked or dipped in the solution before applying the substrate to the wound.

As disclosed above, the substrate may have a retaining string or an x-ray-opaque string attached thereto.

With the method and the hemostatic patch according to the invention, a hemostatic wound treatment is provided according to which an antifibrinolytic agent is applied locally onto a wound. This method and the hemostatic patch stop bleeding very quickly and efficiently in the case of injury-related wounds as well as in the case of surgery. The invention therefore also reduces the time required for operations significantly, and the faster hemostatic action results in an improved medical course of the operation with reduced complications which could otherwise result from the difficulties in affecting blood coagulation in the situation of excessive bleeding during surgery. Already as a result of the reduced operating time the infection risk is reduced. Also improved is the post-operative hemostasis.

DESCRIPTION OF THE PREFERRED EMBODIMENTS

In connection with the following embodiments the invention will be explained in more detail.

EXAMPLE 1

A hemostatic substrate of pure cotton in the form of a surgical sponge is provided and impregnated with a solution of tranexamic acid having a concentration of 100 mg per 1 ml water. The impregnated substrate is packaged in a seal-tight, sterile foil package and thereby protected against moisture loss. The foil package is opened immediately before use. The impregnated substrate is placed onto the bleeding area undergoing surgery. Fresh hemostatic substrates are applied as need. Surprisingly, by employing the impregnated substrates, bleeding stops within a short period of time. Also, bleeding does not start up again when the substrates are removed from the wound. While conventional sponges soaked with physiological saline solution require approximately 60 to 80 sponges to achieve hemostasis of the location being operated on, hemostasis is achieved with the inventive sponges soaked with tranexamic acid already with only about 20 to 40 sponges. At the same time, the need for cauterizing blood vessels by means of bipolar forceps is reduced from 20 to 40 vessels usually requiring cauterization to only about 2 to 4 vessels.

The substrate impregnated with tranexamic acid solution not only reduces the operating time. The faster hemostatic action results in an improved medical course of the operation with reduced complications which could be caused by heavy bleeding and the difficulty in affecting blood coagulation during operation. Improved is also the post-operative hemostasis.

Surprisingly, the substrate according to the invention cannot only be handled easily during operation but also has a positive effect on wound healing.

EXAMPLE 2

A kit comprised of surgical sponges and ampules filled with tranexamic acid solution having a concentration of 100 mg of tranexamic acid per 1 ml water is used. Directly before using a sponge on the surgical wound, in particular, in the situation of a neurosurgical operation, a portion of or the entire surgical sponge is dipped into or soaked in the tranexamic acid solution. The sponge soaked with the tranexamic acid solution is placed onto the operating location. Within a very short period of time the bleeding stops.

The kit is easily manipulated and its use in the operating room is simple. The required manipulations of opening the ampules, dipping the surgical sponges, and applying the surgical sponges can be performed easily and quickly.

In comparison to known measures for achieving hemostasis, which, for example, take up to about 30 minutes, including application of physiological saline solution sponges or cauterizing bleeding vessels, a substantially improved local hemostasis is achieved.

EXAMPLE 3

The local administration of the hemostatic substrate in connection with the inventive method is also possible for cuts, lacerations, abrasions and the like. A substrate as described in Example 1 is placed onto a cut. Within a very short period of time bleeding stops.

EXAMPLE 4

A hemostatic substrate is prepared according to Example 1 but with aprotinin instead of tranexamic acid. A hemostatic substrate of pure cotton in the form of a surgical sponge is provided and impregnated with a solution of aprotinin having a concentration of 500,000 KIU per 50 ml water. By employing these impregnated substrates on a bleeding wound, bleeding stops within a short period of time.

EXAMPLE 5

A hemostatic substrate as described in Example 4 is used on a cut. Within a very short period of time bleeding stops.

Of course, the invention as described can be used in human as well as veterinary medicine for effecting hemostasis.

While specific embodiments of the invention have been shown and described in detail to illustrate the inventive principles, it will be understood that the invention may be embodied otherwise without departing from such principles.

What is claimed is:

1. A method for effecting hemostasis by affecting and maintaining the effects of coagulation of a bleeding wound, comprising the steps of: applying an antifibrinolytic agent to a complementary absorbent porous substrate selected from the group consisting of a medical compress, a patch, a sponge, a pad, a swab, and a dressing to create a hemostatic patch; detachably temporarily mounting the substrate against the wound, the substrate with the antifibrinolytic agent applied thereto being mounted onto the bleeding wound without adhering the substrate to the wound whereby the entire substrate is readily removable, the substrate being free of clot catalyzing reactive components and being free of hemostatic agents except for the antifibrinolytic agent, releasing the antifibrinolytic agent from the substrate into the wound, using the substrate to absorb blood and liquids from the bleeding wound, and simultaneously using the substrate to place the antifibrinolytic agent against the wound to affect and maintain the effects of coagulation as normally conducted by the body and to prevent clot dissolution.

2. The method according to claim 1, wherein several of the substrates with the antifibrinolytic agent applied thereto are placed onto the bleeding wound.

3. The method according to claim 1, wherein the step of applying comprises the steps of preparing a solution of the antifibrinolytic agent and soaking or impregnating the substrate with the solution.

4. The method according to claim 3, wherein the antifibrinolytic agent comprises one or more antifibrinolytic compounds selected from the group consisting of lysine analogs and kinins.

5. The method according to claim 4, wherein the lysine analogs are .epsilon.-aminocaproic acid, tranexamic acid, and p-aminomethyl benzoic acid, and wherein the kinin is aprotinin.

6. The method according to claim 4, wherein, in the step of preparing the solution, a solvent suitable for dissolving the one or more antifibrinolytic compounds is used and wherein the one or more antifibrinolytic compounds are dissolved in an amount effective to provide hemostatic action.

7. The method according to claim 6, wherein the solvent is water or physiological saline and wherein the one or more antifibrinolytic compounds are present in a concentration between 50 mg to 150 mg per 1 ml solvent for lysine analogs and 10,000 to 150,000 KIU per 1 ml solvent for kinins.

8. The method of claim 1 including the step of periodically replacing the combined substrate and antifibrinolytic agent with a fresh substrate and antifibrinolytic agent.

9. The method according to claim 1 wherein the method is used to stop bleeding from wounds resulting from injury and/or surgery.

10. The method according to claim 9 wherein the substrate is a surgical sponge.

11. The method according to claim 1 wherein the substrate is a surgical sponge.

12. A hemostatic patch to affect and maintain the effects of coagulation comprising: an absorbent porous clot promoting substrate selected from the group consisting of a medical compress, a patch, a sponge, a pad, a swab, and a dressing; and a complementary means for effecting hemostasis by affecting coagulation contained within the substrate, wherein the complementary means for effecting hemostasis by affecting coagulation is an antifibrinolytic agent, the substrate being free of clot catalyzing reactive components and being free of hemostatic agents except for the antifibrinolytic agent whereby the substrate comprises means for absorbing blood and liquids from a bleeding wound and for promoting clot formation without sealing any portion of the substrate to the wound by detachably temporarily mounting the substrate to the wound whereby the entire substrate is readily removable, the antifibrinolytic agent being releasably contained within the substrate whereby the antifibrinolytic agent is capable of being released into the wound, the antifibrinolytic agent comprising means for preventing clot dissolution, and the substrate and antifibrinolytic agent in combination being means to affect and maintain the effects of coagulation as normally conducted by the body.

13. The patch according to claim 12, wherein the substrate further comprises an x-ray-opaque string or a retaining string.

14. The patch according to claim 12, wherein the means for preventing clot dissolution comprises one or more antifibrinolytic compounds selected from the group consisting of lysine analogs and kinins, wherein the lysine analogs are .epsilon.-aminocaproic acid, tranexamic acid, and p-aminomethyl benzoic acid, and wherein the kinin is aprotinin.

15. The patch according to claim 14, wherein the antifibrinolytic agent is of a solution comprising a solvent suitable for dissolving the one or more antifibrinolytic compounds and wherein the one or more antifibrinolytic compounds are dissolved in an amount effective to provide hemostatic action.

16. The patch according to claim 15, wherein the solvent is water or physiological saline and wherein the one or more antifibrinolytic compounds are present in a concentration between 50 mg to 150 mg per 1 ml solvent for lysine analogs and 10,000 to 150,000 KIU per 1 ml solvent for kinins.

17. The patch according to claim 8 in combination with a disposable seal-tight envelope in which the hemostatic patch is sealed to be sterile and to stay moist until use.

18. The patch according to claim 12 wherein the substrate is a surgical sponge.

19. A hemostatic medical kit comprising: one or more porous clot promoting substrates selected from the group consisting of a medical compress, a patch, a sponge, a pad, a swab, and a dressing for creating at least one hemostatic patch; and a complementary means for effecting hemostasis by enhancing coagulation, wherein the means for effecting hemostasis by enhancing coagulation is a solution of an antifibrinolytic agent for impregnating the one or more substrates, the antifibrinolytic agent being the sole hemostatic agent in the kit so that when the antifibrinolytic agent is applied to the substrate to form a hemostatic patch the substrate is free of clot catalyzing reactive components and is free of hemostatic agents except for the antifibrinolytic agent whereby the substrate comprises means for absorbing blood and liquids from a bleeding wound without sealing any portion of the substrate to the wound by detachably temporarily mounting the entire substrate to the wound whereby the substrate is readily removable, the antifibrinolytic agent being releasably containable within the substrate whereby the antifibrinolytic agent is capable of being released into the wound, the antifibrinolytic agent comprising means for preventing clot dissolution, and the substrate and antifibrinolytic agent in combination being means to affect and maintain the effects of coagulation as normally conducted by the body.

20. The kit according to claim 19, wherein the substrate further comprises an x-ray-opaque string or a retaining string.

21. The kit according to claim 19, wherein the means for preventing clot dissolution comprises one or more antifibrinolytic compounds selected from the group consisting of lysine analogs and kinins, wherein the lysine analogs are .epsilon.-aminocaproic acid, tranexamic acid, and p-aminomethyl benzoic acid, and wherein the kinin is aprotinin.

22. The kit according to claim 21, wherein the antifibrinolytic agent is a solution comprising a solvent suitable for dissolving the one or more antifibrinolytic compounds and wherein the one or more antifibrinolytic compounds are dissolved in an amount effective to provide hemostatic action, wherein the solvent is water or physiological saline and wherein the one or more antifibrinolytic compounds are present in a concentration between 50 mg to 150 mg per 1 ml solvent for lysine analogs and 10,000 to 150,000 KIU per 1 ml solvent for kinins.

23. The kit according to claim 19 wherein the substrate is a surgical sponge.

24. A hemostatic patch to affect and maintain the effects of coagulation comprising: an absorbent porous clot promoting substrate selected from the group comprising a medical compress, a patch, a sponge, a pad, a swab, and a dressing; and said substrate containing a coagulation enhancing substance for effecting the formation of a clot, said substance consisting of an antifibrinolytic agent, the substrate being free of clot catalyzing reactive components and being free of hemostatic agents except for the antifibrinolytic agent whereby said substrate comprises means to absorb blood and liquids from a bleeding wound without sealing any portion of the substrate to the wound by detachably temporarily mounting the substrate to the wound whereby the entire substrate is readily removable, the antifibrinolytic agent being releasably contained within the substrate whereby the antifibrinolytic agent is capable of being released into the wound, said antifibrinolytic agent functioning to prevent clot dissolution, and the substrate and antifibrinolytic agent in combination being means to affect and maintain the effects of coagulation as normally conducted by the body.

25. The patch according to claim 24, wherein the antifibrinolytic agent is tranexamic acid having a concentration between 50 mg to 150 mg per 1 ml of solvent, and said substrate being a sponge.

26. The patch according to claim 24 wherein the substrate is a surgical sponge.

27. A method for affecting and maintaining the effects of coagulation of a bleeding wound, comprising the steps of: providing an absorbent porous clot promoting substrate selected from the group comprising a medical compress, a patch, a sponge, a pad, a swab, and a dressing; applying a coagulation enhancing substance to the substrate to create a hemostatic patch, wherein the coagulation enhancing substance consists of an antifibrinolytic agent and with the substrate being free of clot catalyzing reactive components and being free of hemostatic agents except for the antifibrinolytic agent; detachably temporarily mounting the substrate with the antifibrinolytic agent applied thereto onto a bleeding wound without adhering any portion of the substrate to the wound whereby the entire substrate is readily removable, releasing the antifibrinolytic agent from the substrate into the wound, using the substrate to absorb blood and liquids from the bleeding wound and simultaneously using the substrate to place the antifibrinolytic agent against the wound to prevent clot dissolution, and the substrate and antifibrinolytic agent affecting and maintaining the effects of coagulation as normally conducted by the body.

28. The method according to claim 27 including the step of periodically replacing the combined substrate and antifibrinolytic agent with a fresh substrate and antifibrinolytic agent.

29. The method according to claim 27 wherein the method is used to stop bleeding from wounds resulting from injury and/or surgery.

30. The method according to claim 29 wherein the substrate is a surgical sponge.

31. The method according to claim 27 wherein the substrate is a surgical sponge.

32. A method for effecting hemostasis by affecting and maintaining the effects of coagulation of a bleeding wound, comprising the steps of: applying tranexamic acid to a complementary absorbent porous substrate selected from the group consisting of a medical compress, a patch, a sponge, a pad, a swab, and a dressing to create a hemostatic patch; detachably temporarily mounting the substrate against the wound, the substrate with the tranexamic acid applied thereto being mounted onto the bleeding wound without adhering the substrate to the wound whereby the entire substrate is readily removable, the substrate being free of clot catalyzing reactive components and being free of hemostatic agents except for the tranexamic acid, releasing the tranexamic acid from the substrate into the wound, using the substrate to absorb blood and liquids from the bleeding wound, and simultaneously using the substrate to place the tranexamic acid against the wound to affect and maintain the effects of coagulation as normally conducted by the body and to prevent clot dissolution.

33. The method according to claim 32, wherein the step of applying comprises the steps of preparing a solution of the tranexamic acid and soaking or impregnating the substrate with the solution.

34. The method according to claim 33, wherein, in the step of preparing the solution, a solvent suitable for dissolving the tranexamic acid is used and wherein the tranexamic acid is dissolved in an amount effective to provide hemostatic action, wherein the solvent is water or physiological saline and wherein the tranexamic acid is present in a concentration between 50 mg to 150 mg per 1 ml solvent, and wherein the substrate is a surgical sponge.

35. The method according to claim 32 including the step of periodically replacing the combined substrate and tranexamic acid with a fresh substrate and tranexamic acid.

36. The method according to claim 32 wherein the method is used to stop bleeding from wounds resulting from injury and/or surgery.

37. A hemostatic patch to affect and maintain the effects of coagulation comprising: an absorbent porous clot promoting substrate selected from the group consisting of a medical compress, a patch, a sponge, a pad, a swab, and a dressing; and a complementary means for effecting hemostasis by affecting coagulation contained within the substrate, wherein the complementary means for effecting hemostasis by affecting coagulation is tranexamic acid, the substrate being free of clot catalyzing reactive components and being free of hemostatic agents except for the tranexamic acid whereby the substrate comprises means for absorbing blood and liquids from a bleeding wound and for promoting clot formation without sealing any portion of the substrate to the wound by detachably temporarily mounting the substrate to the wound whereby the entire substrate is readily removable, the tranexamic acid being releasably contained within the substrate whereby the tranexamic acid is capable of being released into the wound, the tranexamic acid comprising means for preventing clot dissolution, and the substrate and tranexamic acid combination being means to affect and maintain the effects of coagulation as normally conducted by the body.

38. The patch according to claim 37, wherein the substrate further includes an x-ray-opaque string or a retaining string.

39. The patch according to claim 37, wherein the tranexamic acid is in the form of a solution comprising a solvent suitable for dissolving the tranexamic acid which is in an amount effective to provide hemostatic action.

40. The patch according to claim 39, wherein the solvent is water or physiological saline and wherein the tranexamic acid is present in a concentration between 50 mg to 150 mg per 1 ml solvent, and the substrate is a surgical sponge.

* * * * *